US009907902B2

(12) United States Patent
Mitrosky et al.

(10) Patent No.: US 9,907,902 B2
(45) Date of Patent: Mar. 6, 2018

(54) PRECISE ACCURATE MEASUREMENT OF THE ADMINISTRATION OF DRUGS USING THE INJECTION METHOD BY MEANS OF ULTRASONIC PULSE-ECHO PRINCIPLES

(71) Applicant: Maxim Integrated Products, Inc., San Jose, CA (US)

(72) Inventors: Jim Mitrosky, Frisco, TX (US); Roberto Amadio, Milan (IT); Mike Lander, Dallas, TX (US)

(73) Assignee: Maxim Integrated Products, Inc., San Jose, CA (US)

( * ) Notice: Subject to any disclaimer, the term of this patent is extended or adjusted under 35 U.S.C. 154(b) by 313 days.

(21) Appl. No.: 14/557,796

(22) Filed: Dec. 2, 2014

(65) Prior Publication Data
US 2015/0174342 A1 Jun. 25, 2015

Related U.S. Application Data (60) Provisional application No. 61/918,998, filed on Dec. 20, 2013.

(51) Int. Cl.
*A61M 3/00* (2006.01)
*A61M 5/14* (2006.01)
(Continued)

(52) U.S. Cl.
CPC ........ *A61M 5/1411* (2013.01); *A61M 5/1684* (2013.01); *A61M 5/31525* (2013.01);
(Continued)

(58) Field of Classification Search
CPC .. A61M 2205/3389; A61M 2205/3379; A61M 2205/3375; A61M 5/1684; G01F 11/027; G01F 1/7082
See application file for complete search history.

(56) References Cited

U.S. PATENT DOCUMENTS

| 5,705,807 A | 1/1998 | Throngnumchai et al. |
| 6,113,578 A * | 9/2000 | Brown ............... A61B 5/14532 222/23 |

(Continued)

FOREIGN PATENT DOCUMENTS

| DE | 10322718 A1 * | 12/2004 | ......... G01F 23/2962 |
| JP | H10164324 A | 6/1998 | |

OTHER PUBLICATIONS

Y. Ni, et al., "Ambient Light Invariant Camera System for Face Reconginition", Institut National des Télécommunications, Oct. 2011, 7 pages.

*Primary Examiner* — Emily Schmidt (57) ABSTRACT

A dosage control system includes a syringe and a dosage control module. The syringe includes a barrel and a plunger. The plunger includes a plunger seal located within the barrel and the barrel includes an end configured to connect to a needle. The dosage control module measures a first distance between the plunger seal and the end of the barrel, measures at least one second distance between the plunger seal and the end of the barrel, determines whether a predetermined amount of medication has been administered from the syringe based on a difference between the first distance and the at least one second distance, and selectively activates at least one of a visual indication and an audio indication if the predetermined amount of medication has been administered from the syringe.

9 Claims, 7 Drawing Sheets

(51) Int. Cl.
  *A61M 5/168* (2006.01)
  *A61M 5/315* (2006.01)
  *G01F 11/02* (2006.01)
  *A61M 5/36* (2006.01)

(52) U.S. Cl.
  CPC ........... *G01F 11/027* (2013.01); *A61M 5/365* (2013.01); *A61M 2205/0294* (2013.01); *A61M 2205/18* (2013.01); *A61M 2205/3306* (2013.01); *A61M 2205/3375* (2013.01); *A61M 2205/3379* (2013.01); *A61M 2205/3382* (2013.01); *A61M 2205/3389* (2013.01); *A61M 2205/3553* (2013.01); *A61M 2205/43* (2013.01); *A61M 2205/505* (2013.01); *A61M 2205/52* (2013.01); *A61M 2205/581* (2013.01); *A61M 2205/583* (2013.01); *A61M 2205/702* (2013.01); *A61M 2209/01* (2013.01)

(56) References Cited

U.S. PATENT DOCUMENTS

| | | |
|---|---|---|
| 7,023,481 B1 | 4/2006 | Watanabe et al. |
| 7,286,174 B1 | 10/2007 | Weale et al. |
| 8,283,620 B2 | 10/2012 | Raynor et al. |
| 8,333,188 B2 | 12/2012 | Masada et al. |
| 8,350,912 B2 | 1/2013 | Kato |
| 8,715,224 B2 | 5/2014 | Kamen et al. |
| 8,857,269 B2 | 10/2014 | Johnson et al. |
| 9,375,531 B2 | 6/2016 | Lee et al. |
| 2007/0244469 A1 | 10/2007 | Ozeri et al. |
| 2010/0288036 A1* | 11/2010 | Volkwein ............... G01B 17/00 73/114.29 |
| 2012/0232396 A1* | 9/2012 | Tanabe .................... A61B 8/00 600/447 |
| 2012/0312072 A1* | 12/2012 | Stringham ........... G01N 29/032 73/19.03 |
| 2013/0281965 A1 | 10/2013 | Kamen et al. |
| 2013/0310756 A1* | 11/2013 | Whalley ................ A61M 5/31 604/189 |
| 2013/0327827 A1* | 12/2013 | Lautzenhiser ......... G06K 7/042 235/439 |
| 2014/0207080 A1* | 7/2014 | Allerdings ............ A61M 5/168 604/207 |
| 2014/0243750 A1* | 8/2014 | Larsen ................ A61M 5/1452 604/189 |
| 2015/0174330 A1* | 6/2015 | Nagel ................... A61M 5/315 604/218 |

* cited by examiner

PRECISE ACCURATE MEASUREMENT OF THE ADMINISTRATION OF DRUGS USING THE INJECTION METHOD BY MEANS OF ULTRASONIC PULSE-ECHO PRINCIPLES

CROSS-REFERENCE TO RELATED APPLICATIONS

This application claims the benefit of U.S. Provisional Application No. 61/918,998, filed on Dec. 20, 2013. The entire disclosures of the applications referenced above are incorporated herein by reference.

FIELD

The present disclosure relates to systems and methods for automated control of administration of medication via injection.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Medication may be administered to an individual using a syringe. For example, a syringe may be used to inject the medication directly into the individual (e.g., via a subcutaneous injection) and/or into an intravenous (IV) medication supply line. The syringe includes a needle, a barrel, and a plunger. A prescribed amount of the medication is drawn into a barrel of the syringe (e.g., by inserting the needle into a supply of the medication and retracting the plunger). The medication is injected by depressing the plunger to force the medication from the barrel, through the needle, and into an injection site. An amount of medication administered corresponds to a distance the plunger is retracted to draw the medication into the barrel and a distance the plunger is depressed to expel the medication from the barrel.

SUMMARY

A dosage control system includes a syringe and a dosage control module. The syringe includes a barrel and a plunger. The plunger includes a plunger seal located within the barrel and the barrel includes an end configured to connect to a needle. The dosage control module measures a first distance between the plunger seal and the end of the barrel, measures at least one second distance between the plunger seal and the end of the barrel, determines whether a predetermined amount of medication has been administered from the syringe based on a difference between the first distance and the at least one second distance, and selectively activates at least one of a visual indication and an audio indication if the predetermined amount of medication has been administered from the syringe.

A dosage control method includes transmitting a first plurality of voltage pulses to a piezoelectric transducer arranged on a syringe, receiving, based on the first plurality of voltage pulses, a second plurality of voltage pulses from the syringe, determining an amount of time between a first voltage pulse and at least one second voltage pulse of the second plurality of voltage pulses, and determining, based on the amount of time, at least one of an amount of medication administered from the medication delivery device and whether air bubbles are present in the medication within the medication delivery device. The method further includes selectively activating at least one of a visual indication and an audio indication based on the determination.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

A dosage control system according to the principles of the present disclosure accurately administers a correct dosage of a medication using a syringe or other medication delivery device. For example, the dosage control system may measure an amount that a plunger is moved within a barrel of a syringe. A distance that the plunger is retracted from the barrel is indicative of an amount of the medication that is drawn into the syringe. Conversely, a distance that the plunger is pressed into the barrel is indicative of an amount of the medication that is administered to an individual. Accordingly, the dosage control system determines an amount of the medication that is drawn into the syringe and/or administered to the individual based on the distance that the plunger is retracted from the barrel and/or the distance that the plunger is pressed into the barrel. For example only, the dosage control system implements pulse-echo acoustic time-of-flight calculation to determine the distance that the plunger travels within the barrel of the syringe.

Figure 1:
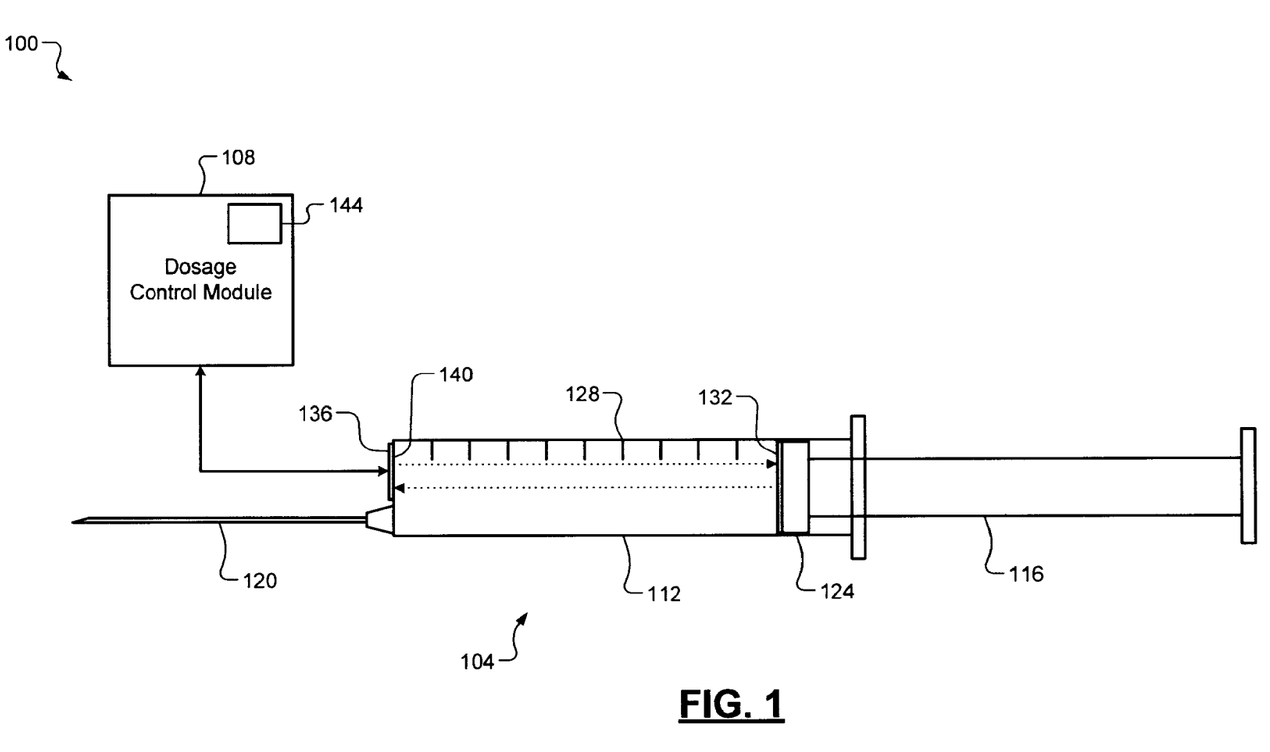
FIG. 1 illustrates an example dosage control system according to the present disclosure.

Referring now to FIG. 1, a dosage control system 100 according to the principles of the present disclosure includes a syringe 104 and a dosage control module 108. The syringe includes a barrel 112, a plunger 116, and a needle 120. Medication is drawn through the needle 120 into the barrel 112 when the plunger 116 is withdrawn from the barrel 112. Conversely, medication is administered through the needle when the plunger 116 is pressed into the barrel 112. For example, the plunger 116 includes a plunger seal 124 that forces the medication from the barrel 112 and through the needle 120 as the plunger 112 is pressed. The barrel 112 may include a scale 128 that provides a visual indication of an amount that the plunger 116 is withdrawn from the barrel 112 (and, accordingly, an amount of medication that is drawn into the barrel 112 and/or administered through the needle 120).

The plunger seal 124 includes a reflective surface 132. For example only, the reflective surface 132 may include metallic foil (e.g., aluminum), stainless steel, an ultrasonic reflector, or any other suitable material able to reflect acoustic pulses. A piezoelectric transducer 136 is provided at an end 140 of the barrel 112 opposite the reflective surface 132. For example only, the transducer 136 may be attached to an inner surface of the end 140, an outer surface of the end 140, and/or embedded within the material of the end 140 (i.e., embedded within plastic or other material of the end 140 of the barrel 112). Although typically centrally located in the end 140 of the barrel 112, the needle 120 may be positioned as shown (e.g., raised/lowered with respect to a central axis of the barrel 112) to accommodate the transducer 136.

The dosage control module 108 determines an amount of medication drawn into the barrel 112 and an amount of medication administered through the needle 120 based on a distance (and/or a change in the distance) between the end 140 of the barrel 112 and the reflective surface 132. For example, the dosage control module 108 measures the distance between the end 140 and the reflective surface 132, which is indicative of the volume within the barrel 112 (e.g. area of a cross section of the barrel 112 multiplied by the distance between the end 140 and the reflective surface 132 equals the volume within the barrel 112).

As the plunger 116 is withdrawn from the barrel 112, the volume (and the amount of medication) increases. Conversely, as the plunger 116 is pressed into the barrel 112, the volume (and the amount of medication) decreases. Accordingly, the dosage control module 108 calculates the volume of medication being drawn into the barrel 112 as the plunger 116 is withdrawn, and then subsequently calculates the volume of the medication administered to an individual as the plunger 116 is pressed into the barrel 112. In other words, the dosage control module 108 measures changes in the distance between the end 140 and the reflective surface 132 to calculate medication dosage.

For example, the dosage control module 108 measures changes in the distance based on a pulse-echo time. The dosage control module 108 transmits a pulse train (for example only, 3V peak-to-peak voltage pulses, 50% duty cycle, 1 MHz) to the transducer 136, causing the transducer 136 to emit a sinusoidal, ultrasonic pulse (e.g., at 1 MHz). The pulse travels through the barrel 112 (i.e., through a medium contained within the barrel 112), reflects off of the reflective surface 132, returns to the transducer 136. The dosage control module 108 receives a return pulse indicative of the pulse returned at the transducer 136. A time between the pulse being transmitted from the transducer 136, reflected off of the reflective surface 132, and returned to the transducer 136 is indicative of the distance between the end 140 and the reflective surface 132. For example, the transducer 136 converts the returned pulse into a voltage pulse that is transmitted back to the dosage control module 108. Accordingly, the dosage control module 108 can dynamically calculate the distance as the plunger 116 is moved within the barrel 112.

The syringe 104 and/or the dosage control module 108 may provide, based on the measured change in the distance between the end 140 and the reflective surface 132, a visual and/or audio indication of when the proper (i.e., a predetermined) dosage amount has been drawn into the barrel 112 and/or administered via the needle 120. For example, the indication may include a display on the dosage control module and/or one or more LEDs that are activated (e.g., a green LED that is activated as the plunger 116 is withdrawn and pressed, and a red LED that is activated and/or a beeping sound that is activated when the distance indicates that the proper amount of medication has been administered). In some implementations, the dosage control module 108 may include a user interface 144 that includes a display, an audio output device (e.g., a speaker), and/or an input mechanism (e.g., buttons, a touchscreen, etc.), or may be connected to another electronic device that provides the user interface 144 for communicating with the dosage control module 108 (e.g. a laptop, mobile device, etc.)

A user may view and input information using the user interface 144. For example, the user may input the type of medication, the dosage amount, patient information, information about the syringe (size, type, volume, etc.) and/or any other suitable information. For example, the dosage control module 108 may be calibrated based on the type of medication. Because the type of medication may affect the medium (i.e., the medium that the ultrasonic pulses is travelling through within the barrel 112), a duration for each pulse to travel between the end 140 and the reflective surface 132 may be affected. Accordingly, the dosage control module 108 may automatically adjust calculations based on the type of medication. Additionally or alternatively, the dosage control module 108 may automatically self-calibrate when the medication is in the syringe 104. For example, if the plunger 116 is in a known position while the barrel 112 contains medication (e.g., fully withdrawn), then the dosage control module 108 can transmit a series of calibration pulses to determine a duration for the pulses to travel through the medium a known distance, and then calibrate the calculation accordingly.

The dosage control module 108 may store information about the medication, dosage, patient, etc. and provide the visual and/or audio indications (e.g. via the user interface 144 and/or LEDs as described) according to the stored information and the operation of the syringe 104, and may update the information according to how much of the medication was actually administered, the individual that administered the medication, the time the medication was administered, etc. In some implementations, the information is stored in, transmitted to, and/or retrieved from a remote location (e.g., a remote server, a cloud or network infrastructure, etc.). For example, a prescribing physician may input data corresponding to medication, dosage amount, patient, etc. at a remote location (e.g., at another location within a hospital, via a mobile device/smartphone, or another suitable device). The data may be electronically stored in a location accessible (e.g., wirelessly) by the dosage control module 108 or automatically transmitted to the dosage control module 108. In this manner, the dosage control module 108 may be automatically (e.g., periodically) updated with accurate information about proper dosages for one or more medications to be administered to specific patients, and may provide indications to the individual administering the medications accordingly.

In some implementations, the dosage control module 108 may provide warnings, based on the measured amount of medication given, to the individual administering the medications and/or other individuals (a prescribing physician, nurse's station, etc.). For example, the dosage control module 108 may provide the warnings if the measured dosage that was administered was less than and/or exceeded a prescribed amount.

Figure 2:
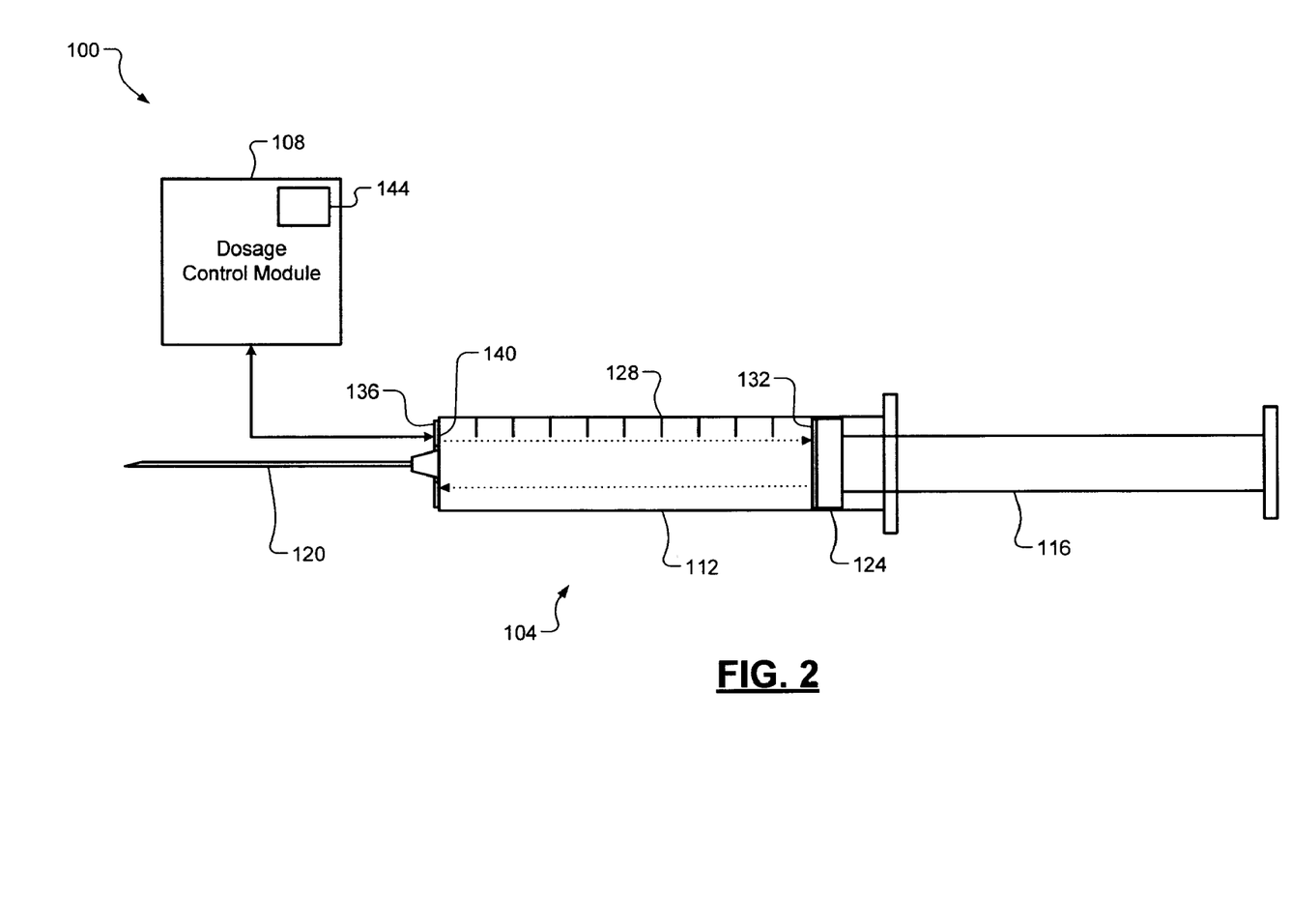
FIG. 2 illustrates another example dosage control system according to the present disclosure.
Figure 3:
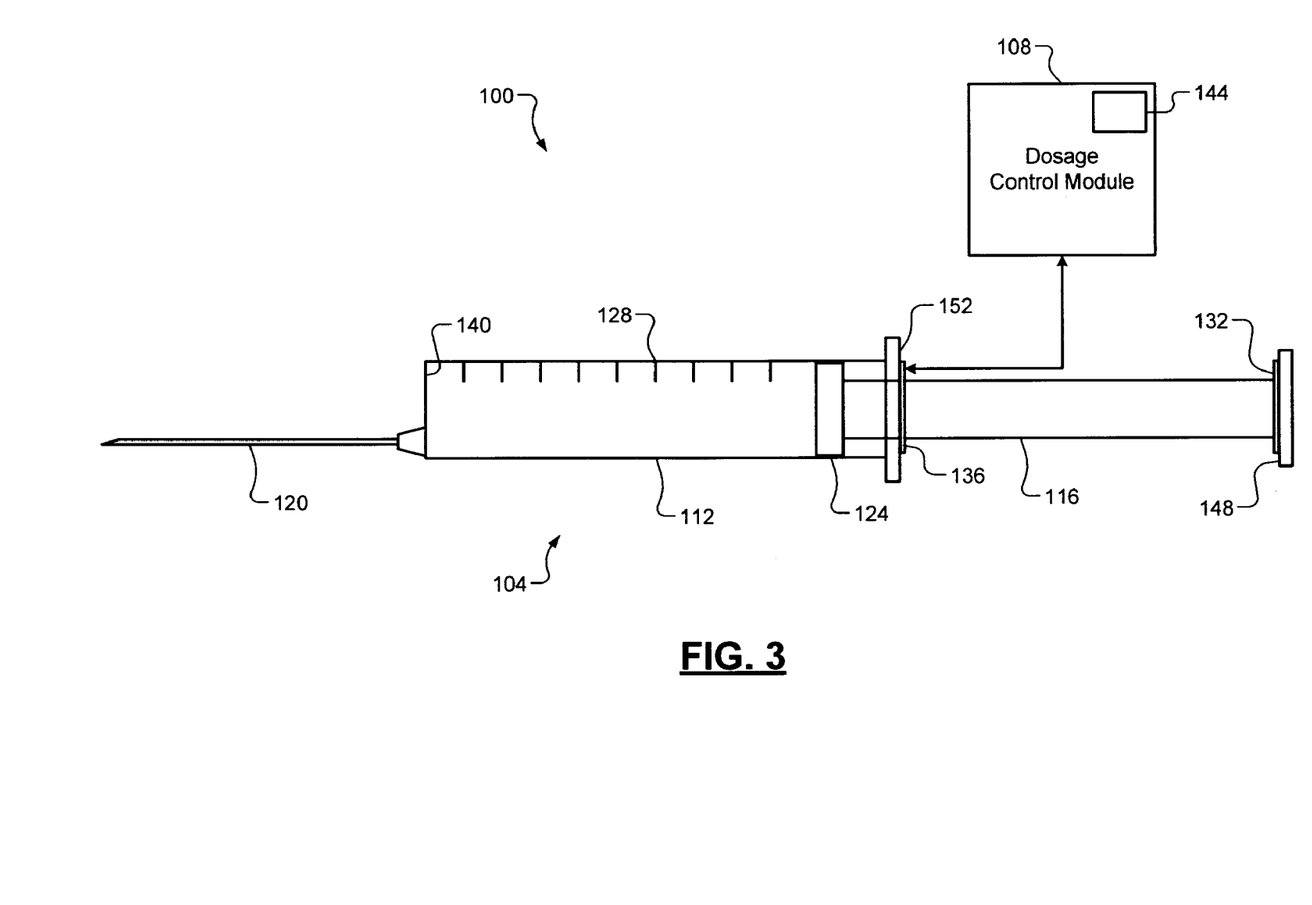
FIG. 3 illustrates another example dosage control system according to the present disclosure.

Referring now to FIGS. 2 and 3, other example dosage control systems 100 are shown. In FIG. 2, the needle 120 is centrally located in the end 140 of the barrel 112 and the transducer 136 encircles the needle 120. In FIG. 3, the reflective surface 132 is located on an inner surface of a top 148 of the plunger 116 and the transducer 136 is located on a top 152 of the syringe.

Figure 4:
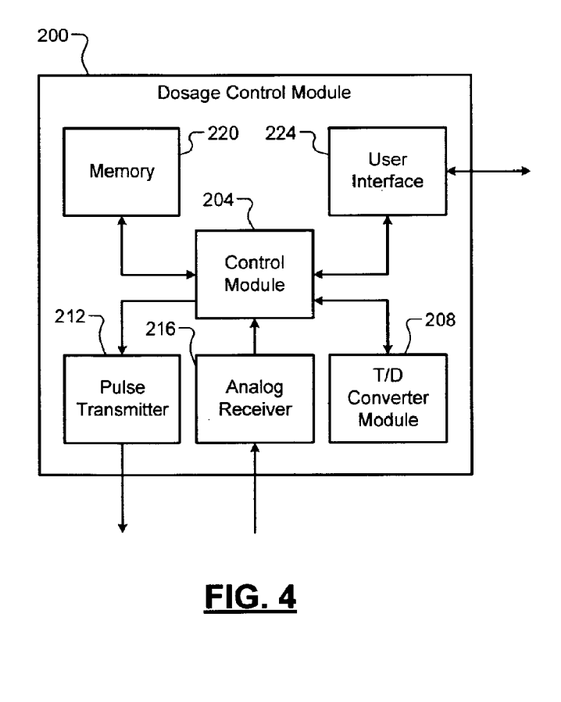
FIG. 4 illustrates an example dosage control module according to the present disclosure.

Referring now to FIG. 4, an example dosage control module 200 includes a control module 204, a time-to-digital (T/D) converter module 208, a pulse transmitter 212, an analog receiver module 216, memory 220, and a user interface 224. The dosage control module 200 may include other components (not shown) such as a wireless or wired communication interface.

The pulse transmitter 212 transmits voltage pulses as described in FIG. 1. The analog receiver module 216 receives voltage pulses transmitted by the transducer 136 in response to return pulses. The T/D converter module 208 calculates the time between the voltage pulses received by the analog receiver module 216. The control module 200, which includes, for example only, a special purpose processor and/or microcontroller, calculates changes in the distance between the reflective surface 132 and the end 140 of the barrel 112 based on the time between pulses calculated by the T/D converter module, controls transmission of the voltage pulses by the pulse transmitter 212, and performs other control functions associated with the operation of the dosage control module. The memory 220 stores information associated with the dosage control module 200 as described in FIG. 1. A user may interact with the dosage control module using the user interface 224.

Figure 5:
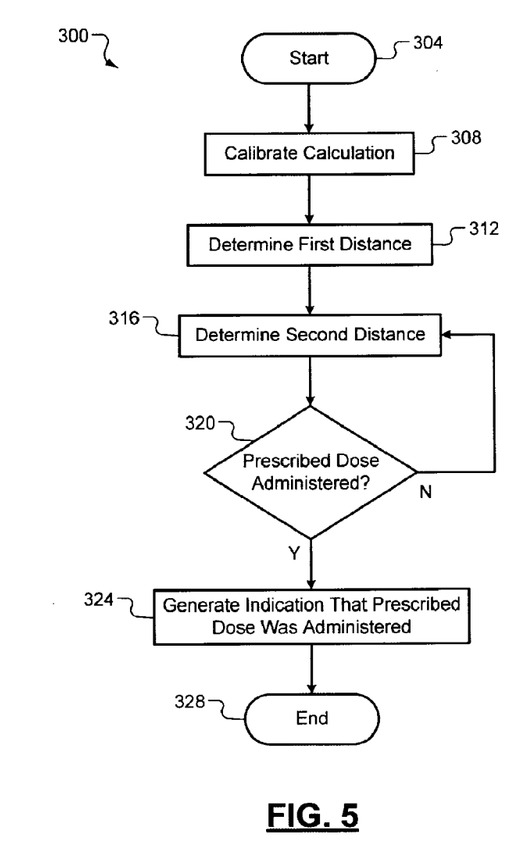
FIG. 5 is a flow diagram illustrating an example dosage control method according to the present disclosure.

Referring now to FIG. 5, an example dosage control method 300 begins at 304. At 308, the method 300 calibrates the calculation. For example, the method 300 determines the transmission medium (for medication already disposed within a loaded syringe) and/or self-calibrates by transmitting calibration pulses. At 312, the method 300 determines an amount the plunger is withdrawn from the barrel based on a first distance between an end of the barrel and a reflective surface positioned on the plunger seal. At 316, the method 300 determines an amount the plunger has been pressed based on a second distance between the end of the barrel and the reflective surface. At 320, the method 300 determines whether a difference between the first distance and the second distance corresponds to a volume that is equal to or greater than a prescribed dose of the medication. If true, the method 300 continues to 324. If false, the method 300 continues to 316. At 324, the method 300 generates a visual and/or audio indication that the prescribed dose of the medication has been administered. The method 300 ends at 328.

Figure 6:
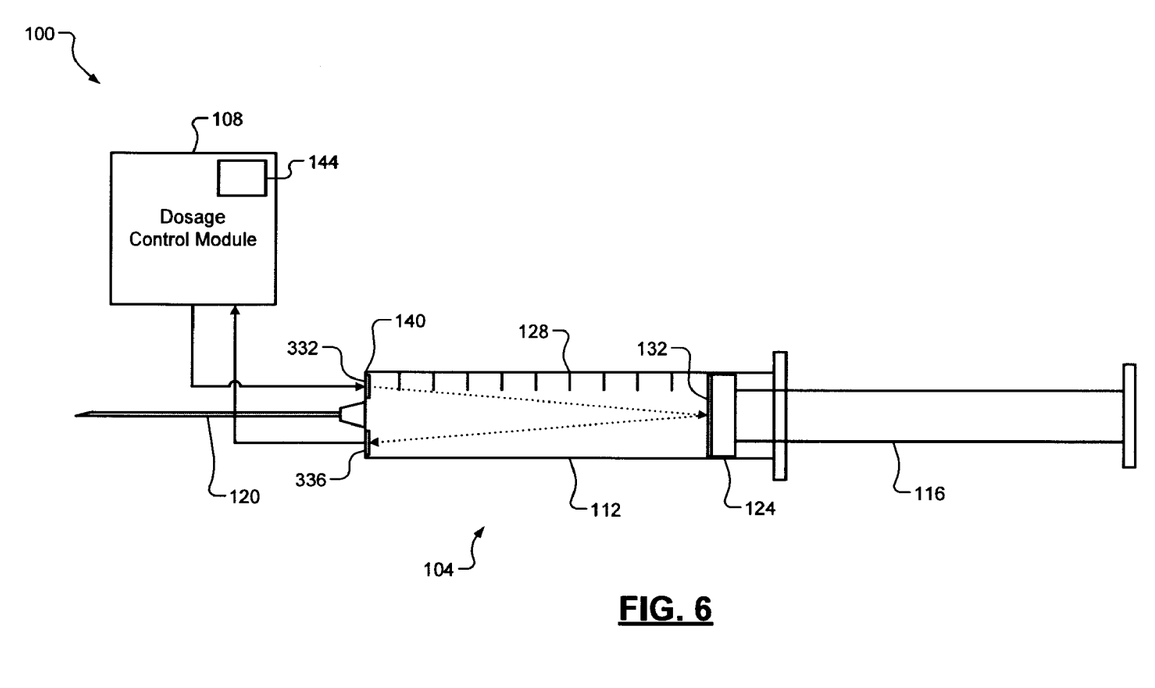
FIG. 6 illustrates another example dosage control system according to the present disclosure.

Referring now to FIG. 6, another example dosage control system 100 is shown. In FIG. 6, separate transmit 332 and receive 336 sensors are provided (e.g., instead of a single transducer) within the syringe 104 at the end 140 of the barrel 112. The dosage control module 108 transits the pulse train via the transmit sensor 332, which transmits a pulse. The pulse reflects off of the reflective surface 132 and is received by the receive sensor 336. In response to receiving the reflected pulse, the receive sensor 336 provides a return pulse to the dosage control module 108.

Figure 7:
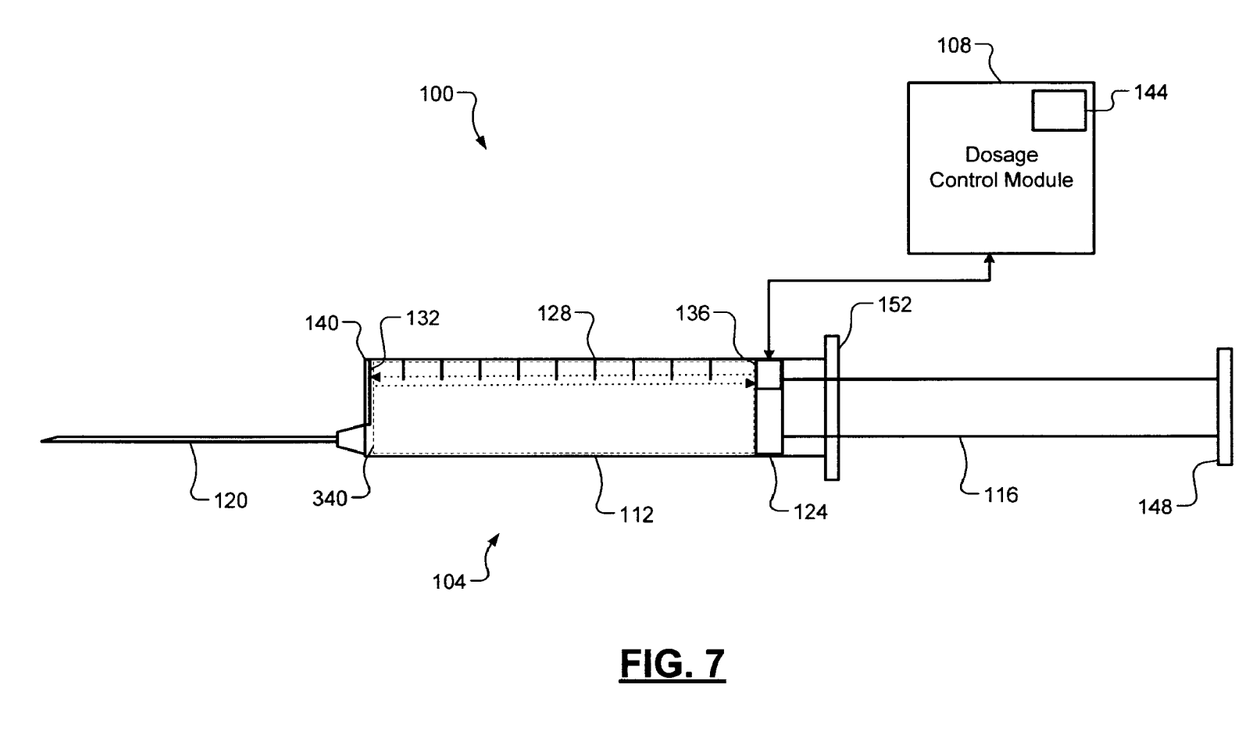
FIG. 7 illustrates another example dosage control system according to the present disclosure.

Referring now to FIG. 7, another example dosage control system 100 is shown. The syringe 104 may be configured to accept a disposable medicine cartridge 340 within the barrel 112. For example, after the medicine in the cartridge 340 is administered, the cartridge 340 may be removed and replaced with another cartridge. Accordingly, the syringe 104 may be reusable. The transducer 136 may be located in or on the plunger 116, such as, for example only, in the plunger seal 124. The reflective surface 132 is located at the end 140 of the barrel 112.

Although several embodiments described herein implement the principles of the present disclosure within a syringe, the dosage control system 100 may be used with other medication delivery mechanisms or devices (e.g., a pen injector, an infusion pump, a nebulizer, etc.). For example, referring now to FIG. 8, the dosage control system 100 may be used with an intravenous (IV) drip system 344. In the IV drip system 344, fluid (i.e., the medicine to be administered) 348 is contained within a drip chamber 352. Gravity causes the fluid 348 to be slowly administered via an IV tube 356. As the fluid 348 is administered, an upper level 360 of the fluid 348 drops.

Figure 8:
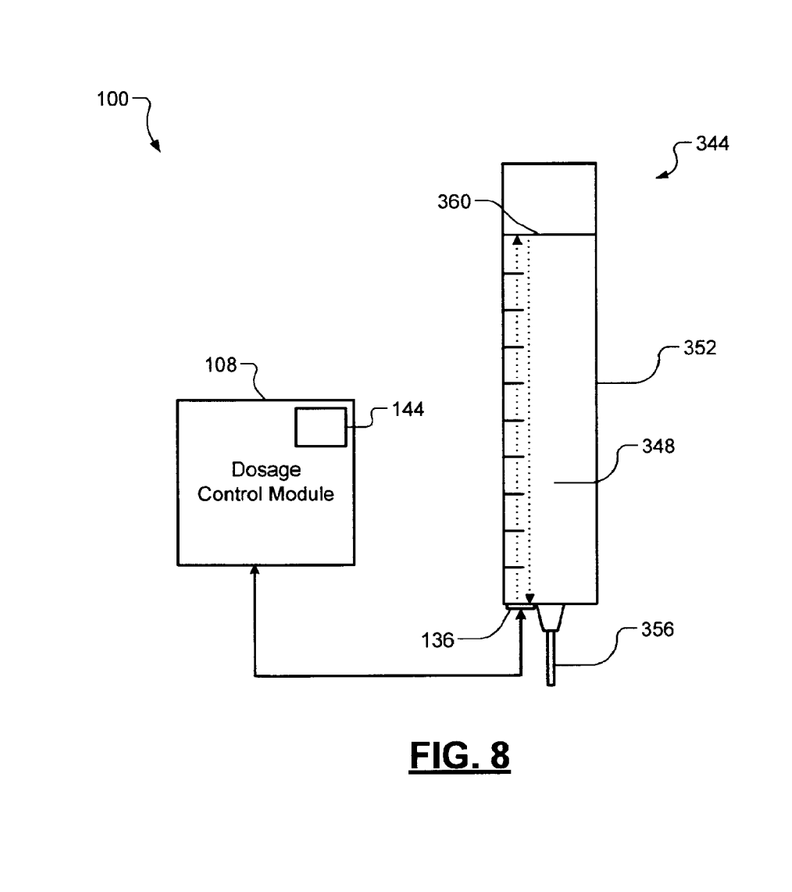
FIG. 8 illustrates another example dosage control system according to the present disclosure.

The transducer 136 is located at a lower end of the drip chamber 352 and transmits pulses upward through the fluid 348 in response to pulses received from the dosage control module 108, and provides return pulses to the dosage control module 108, as described above in other embodiments. Accordingly, as the upper level 360 of the fluid 348 drops, an amount of time between the return pulses also drops, thereby indicating the amount of the fluid 348 remaining in the drip chamber 352 (and the amount of the fluid 348 administered).

Figure 9:
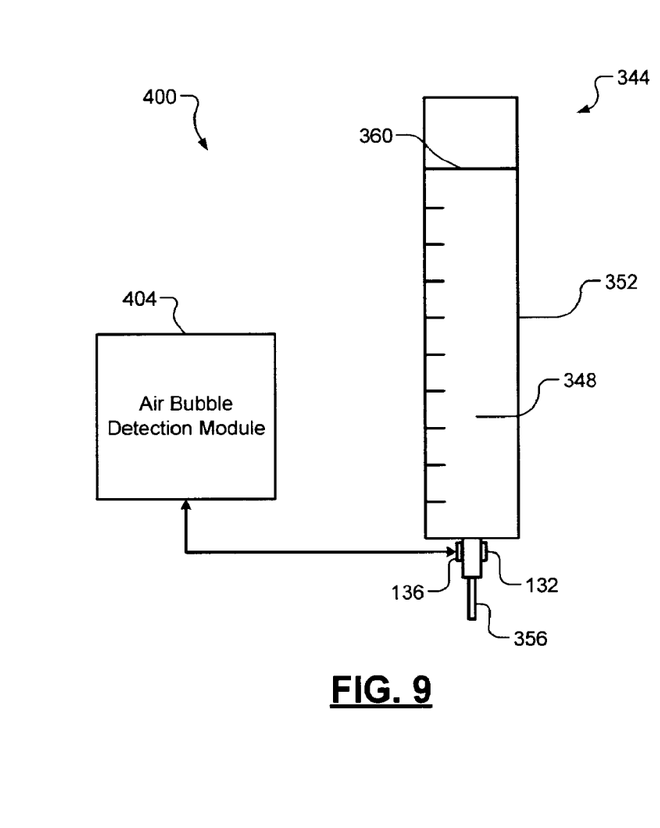
FIG. 9 illustrates an example air bubble detection system according to the present disclosure.

Referring now to FIG. 9, the principles of the present disclosure may also be implemented in an air bubble detection system 400. The air bubble detection system 400 includes an air bubble detection module 404. The air bubble detection module 404 may include similar components and functions as the dosage control module 108 as described in FIGS. 1-8, or the dosage control module 108 may be configured to operate in a similar manner as the air bubble detection module 404 as described below. However, instead of (or in addition to) measuring a time between return pulses to determine an amount of medicine administered, the air bubble detection module 404 (and/or the dosage control module 108) measures a time between return pulses to detect air bubbles in the medicine.

For example, the air bubble detection module 404 communicates with a transducer 136 disposed on an IV tube 356 or other portion of an IV drip system 344. Although the air bubble detection system 400 is shown implemented with an IV drip system 344, the air bubble detection system 400 may be used with other medication delivery mechanisms.

The transducer 136 transmits pulses through the IV tube 356 and the medium contained therein. A reflective surface 132 (e.g., an ultrasonic reflector) arranged on a side of the IV tube 356 opposite the transducer 136 reflects return pulses to the transducer 136, which provides the return pulses to the air bubble detection module 404.

The air bubble detection module 404 determines whether air bubbles are present within the medium based on the return pulses. For example, the pulses travel through fluid at a different rate than through air (i.e., air bubbles). Accordingly, the time between the return pulses when there are air bubbles present will be different from the time between the return pulses when there are no air bubbles present. In this manner, the air bubble detection module 404 detects air bubbles within the IV tube 356 based on changes in the time between the return pulses. In response to detecting air bubbles, the air bubble detection module 404 may, for example only, alert a user or patient that the air bubbles have been detected, discontinue delivery of the fluid to the patient, and/or perform other suitable functions.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. §112(f) unless an element is expressly recited using the phrase "means for," or in the case of a method claim using the phrases "operation for" or "step for."

What is claimed is:

1. A dosage control system comprising:
a syringe including a barrel and a plunger, wherein the plunger includes a plunger seal located within the barrel, and wherein the barrel includes an end configured to connect to a needle, wherein
the plunger seal includes a reflective surface, wherein the reflective surface (i) is located within the barrel opposite the end configured to connect to the needle and (ii) faces the end of the barrel configured to connect to the needle, and
the end of the barrel configured to connect to the needle includes a piezoelectric transducer arranged to transmit a plurality of sound pulses from the end of the barrel configured to connect to the needle, through medication contained within the barrel, and toward the plunger seal, wherein the piezoelectric transducer is attached to an inner surface of the end of the barrel; and
a dosage control module that determines the type of the medication contained within the barrel of the syringe and, based on (i) the determined type of the medication contained within the barrel of the syringe and (ii) the sound pulses transmitted through the medication, measures a first distance between the plunger seal and the end of the barrel configured to connect to the needle, measures at least one second distance between the plunger seal and the end of the barrel configured to connect to the needle, determines whether a predetermined amount of medication has been administered from the syringe based on a difference between the first distance and the at least one second distance, and selectively activates at least one of a visual indication and an audio indication if the predetermined amount of medication has been administered from the syringe.

2. The dosage control system of claim 1, wherein the dosage control module measures the first distance and the at least one second distance based on an amount of time for the plurality of sound pulses to travel between the end of the barrel configured to connect to the needle and the plunger seal.

3. The dosage control system of claim 2, wherein the dosage control module transmits a plurality of voltage pulses to the piezoelectric transducer, the piezoelectric transducer converts the plurality of voltage pulses into the plurality of sound pulses, and the plurality of sound pulses are reflected back to the piezoelectric transducer from the reflective surface.

4. The dosage control system of claim 2, wherein the dosage control module includes a time-to-digital converter that calculates the amount of time.

5. The dosage control system of claim 1, wherein the dosage control module determines the type of the medication contained within the barrel of the syringe using information input via a user interface.

6. The dosage control system of claim 1, wherein the dosage control module:
  transmits a series of calibration pulses with the plunger in a known position to determine a duration for the calibration pulses to travel through the medication; and
  measures the first distance between the plunger seal and the end of the barrel configured to connect to the needle and measures the at least one second distance between the plunger seal and the end of the barrel configured to connect to the needle based on the determined duration for the calibration pulses to travel through the medication with the plunger in the known position.

7. The dosage control system of claim 6, wherein the known position is a fully withdrawn position of the plunger.

8. The dosage control system of claim 1, wherein (i) the first distance corresponds to an amount the plunger is withdrawn to draw the medication into the barrel and (ii) the second distance corresponds to an amount the plunger is pressed to administer the medication from the barrel.

9. The dosage control system of claim 1, further comprising an air bubble detection module that determines whether air bubbles are present within the medication based on the sound pulses transmitted through the medication.

* * * * *

UNITED STATES PATENT AND TRADEMARK OFFICE
CERTIFICATE OF CORRECTION

PATENT NO. : 9,907,902 B2  
APPLICATION NO. : 14/557796  
DATED : March 6, 2018  
INVENTOR(S) : Jim Mitrosky et al.

Page 1 of 1

It is certified that error appears in the above-identified patent and that said Letters Patent is hereby corrected as shown below:

On the Title Page

Item (56), Other Publications, Column 2, Line number 2, delete "Reconginition" and insert --Recognition--

In the Specification

At Column 3, Line number 3, delete "112" and insert --116--

At Column 5, Line number 23, delete "200" and insert --204--

Signed and Sealed this  
Nineteenth Day of June, 2018

Andrei Iancu  
*Director of the United States Patent and Trademark Office*